United States Patent [19]
Botich et al.

[11] Patent Number: 6,077,244
[45] Date of Patent: Jun. 20, 2000

[54] CATHETER INSERTION DEVICE WITH RETRACTABLE NEEDLE

[75] Inventors: Michael J. Botich, Oxnard; Thor R. Halseth, Simi Valley, both of Calif.

[73] Assignee: MDC Investment Holdings, Inc., Wilmington, Del.

[21] Appl. No.: 09/070,829

[22] Filed: Apr. 30, 1998

Related U.S. Application Data

[66] Substitute for application No. 60/065,347, Nov. 12, 1997.

[51] Int. Cl.⁷ ..................................................... A61M 5/00
[52] U.S. Cl. ........................... 604/110; 604/164; 604/263
[58] Field of Search ..................................... 604/110, 111, 604/161, 162, 164, 165, 168, 171, 191, 198, 263, 272; 606/108

[56] References Cited

U.S. PATENT DOCUMENTS

| | | |
|---|---|---|
| 4,747,831 | 5/1988 | Kulli . |
| 5,092,853 | 3/1992 | Couvertier, II . |
| 5,338,305 | 8/1994 | Plyley . |
| 5,346,480 | 9/1994 | Hess . |
| 5,433,712 | 7/1995 | Stiles . |
| 5,496,274 | 3/1996 | Graves . |
| 5,501,675 | 3/1996 | Erskine . |
| 5,514,100 | 5/1996 | Mahurkar . |
| 5,562,629 | 10/1996 | Haughton . |
| 5,562,634 | 10/1996 | Flumene . |
| 5,683,368 | 11/1997 | Schmidt . |
| 5,697,907 | 12/1997 | Gaba . |

*Primary Examiner*—Corrine McDermott
*Assistant Examiner*—Patricia M Bianco
*Attorney, Agent, or Firm*—Dann, Dorfman, Herrell and Skillman; Stephen H. Eland

[57] ABSTRACT

A catheter insertion device is provided for inserting an over-the-needle catheter. The device includes an insertion needle that is retractable into the housing of the device after use to prevent exposure to the contaminated needle. A needle retainer releasably retains the needle in an extended position against the rearward bias of the biasing element. The needle retainer engages the hub of the catheter so that when the catheter is removed from the insertion device, the needle retainer automatically releases the needle. The biasing element then propels the needle rearwardly into the housing of the device.

52 Claims, 12 Drawing Sheets

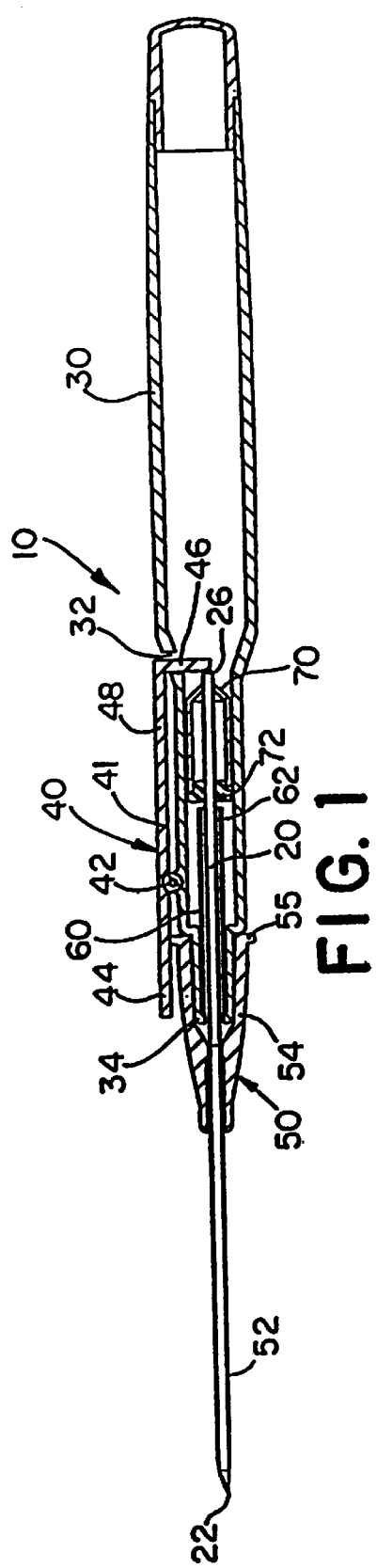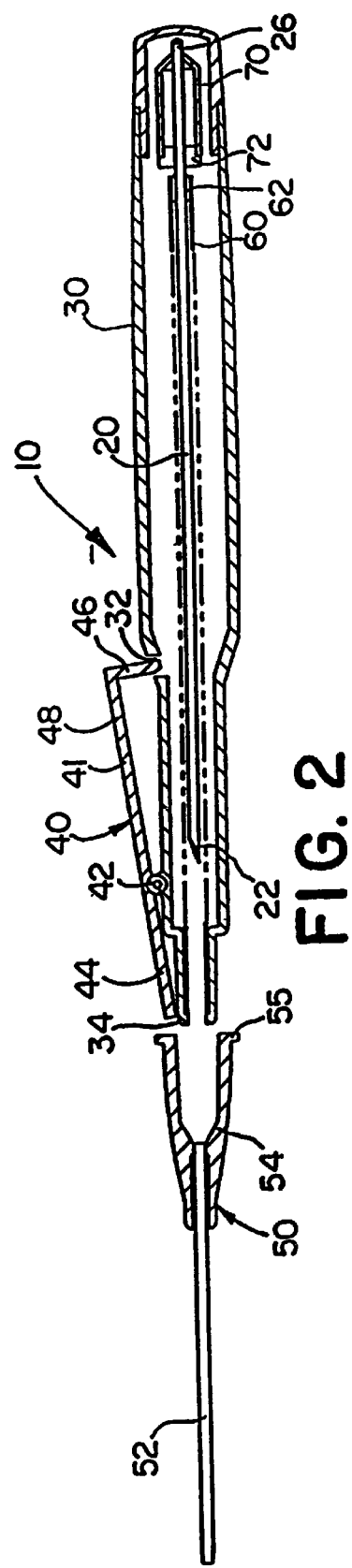

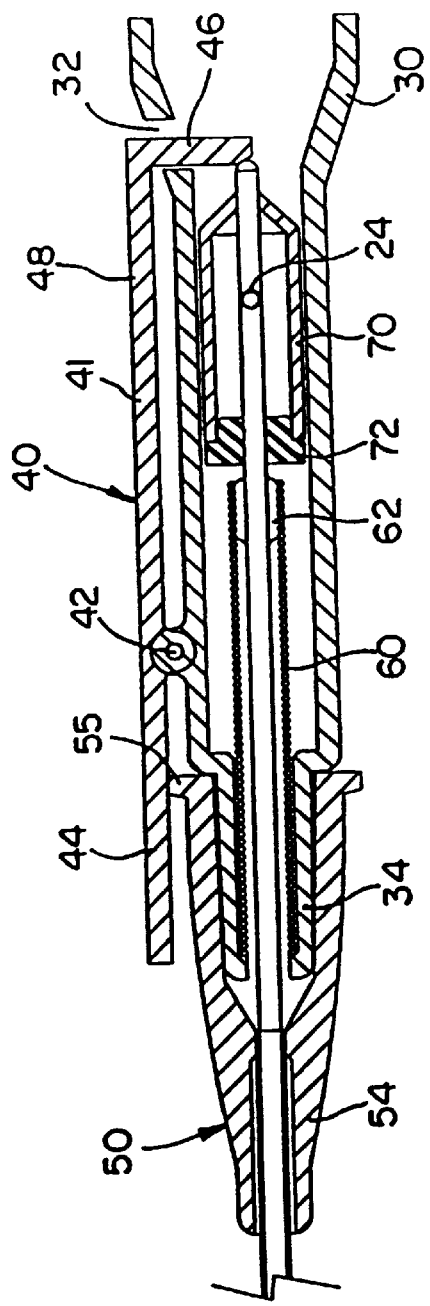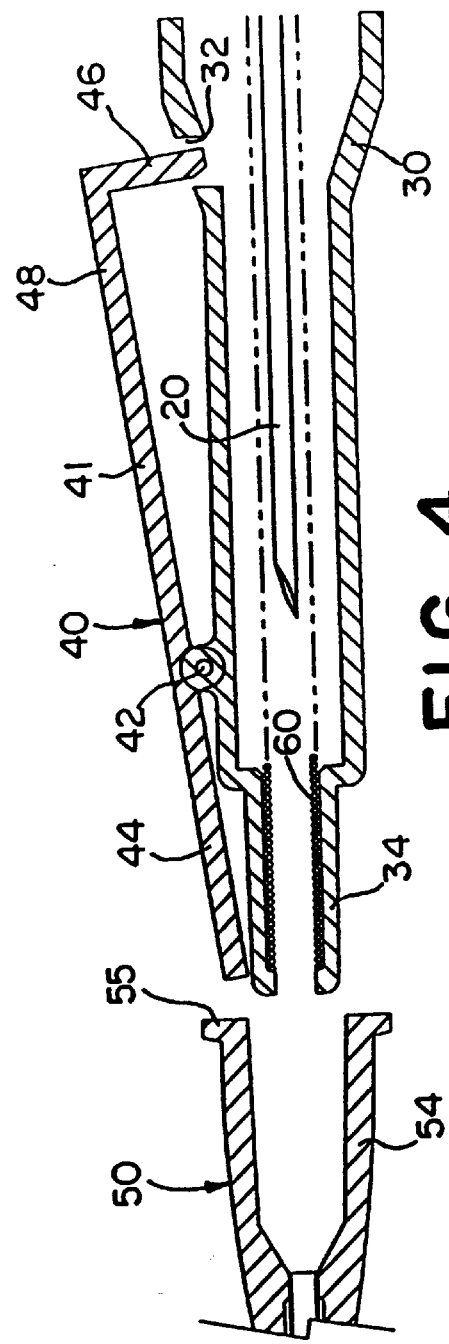

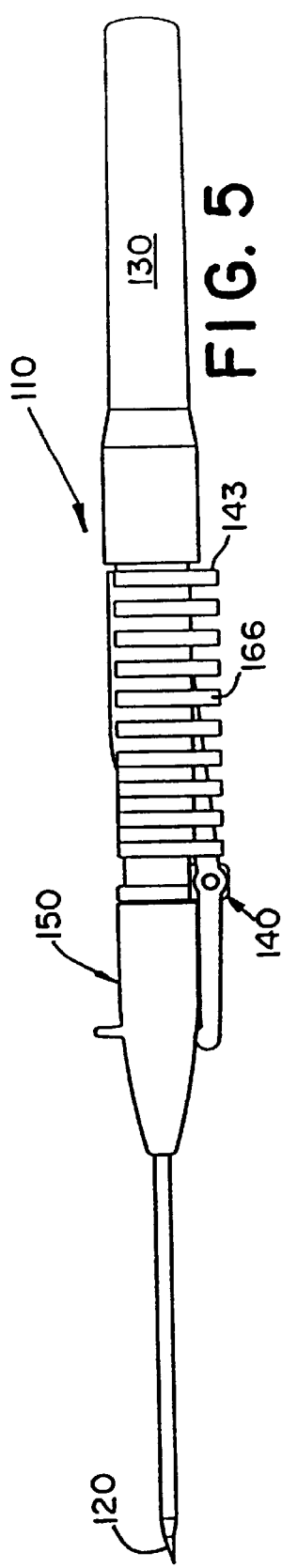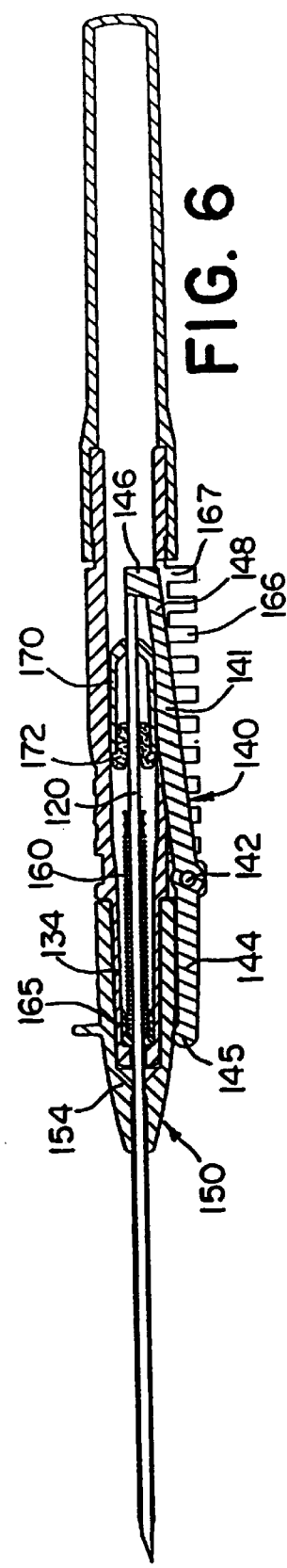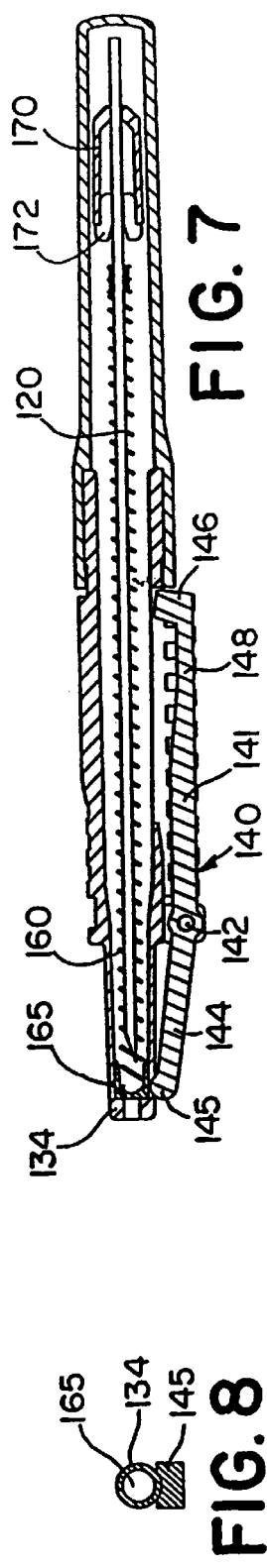

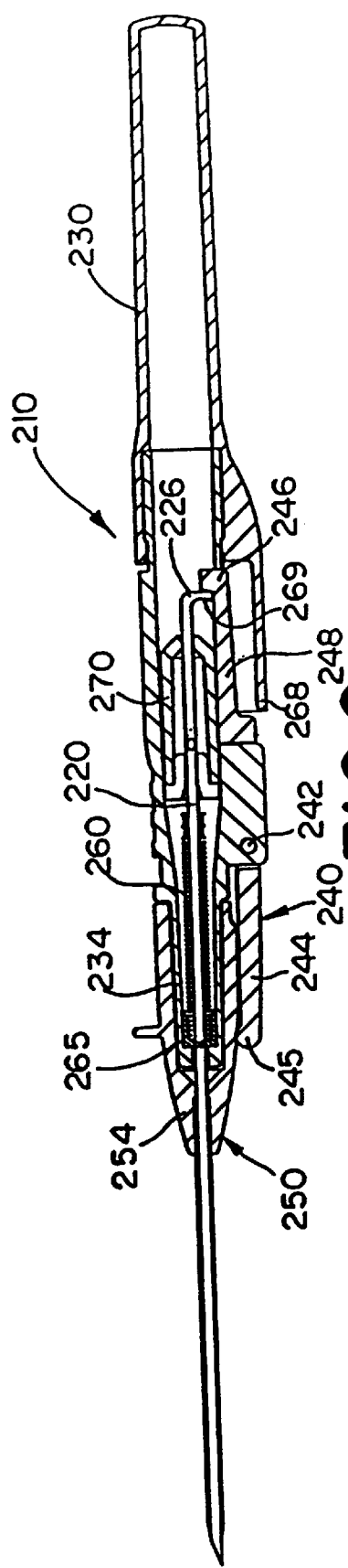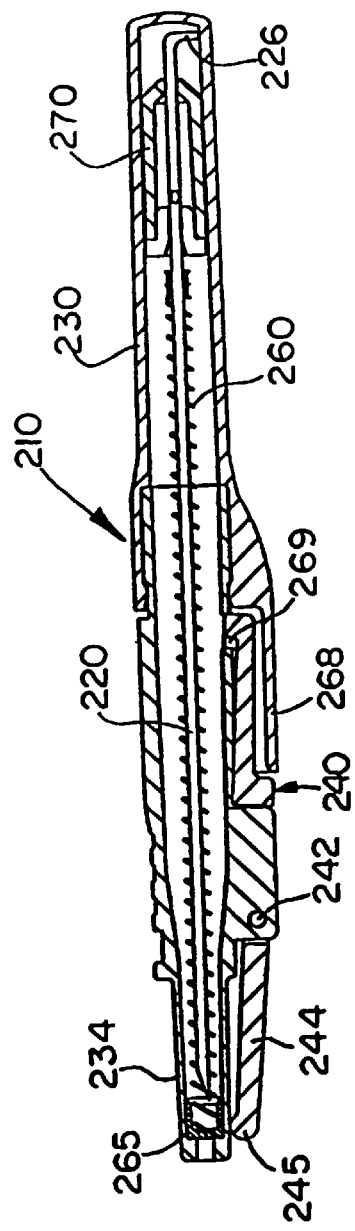

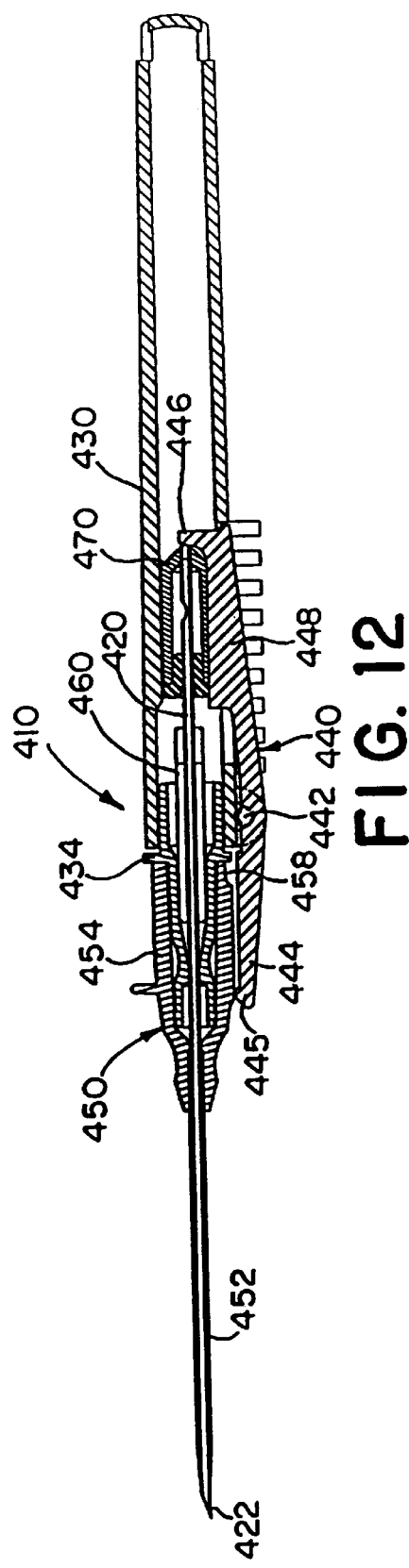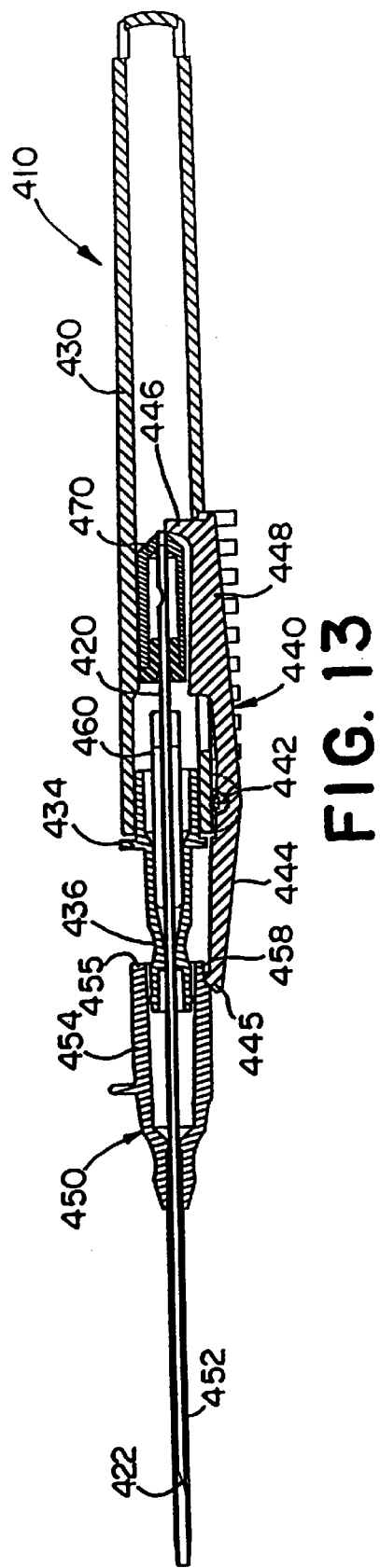

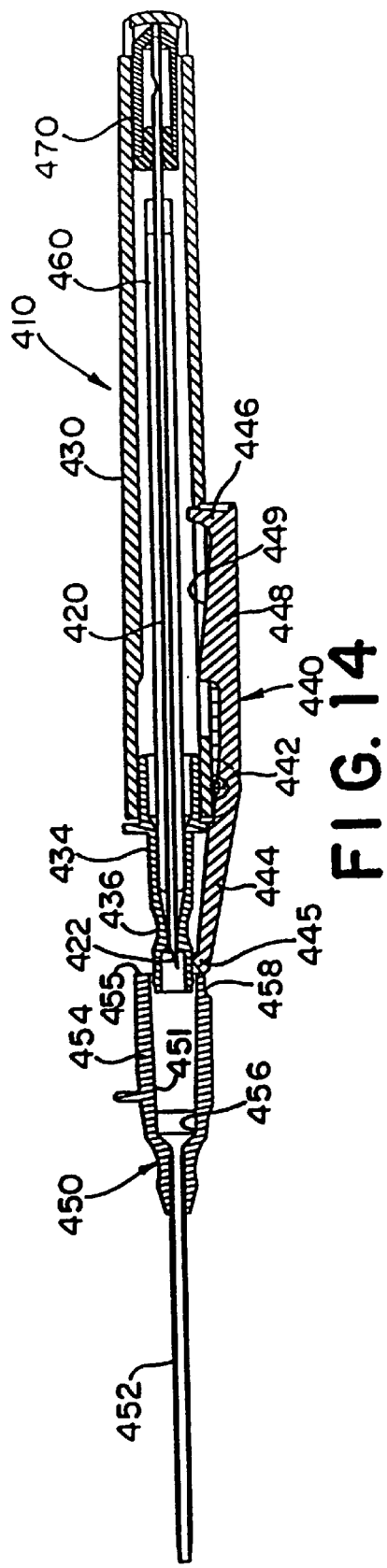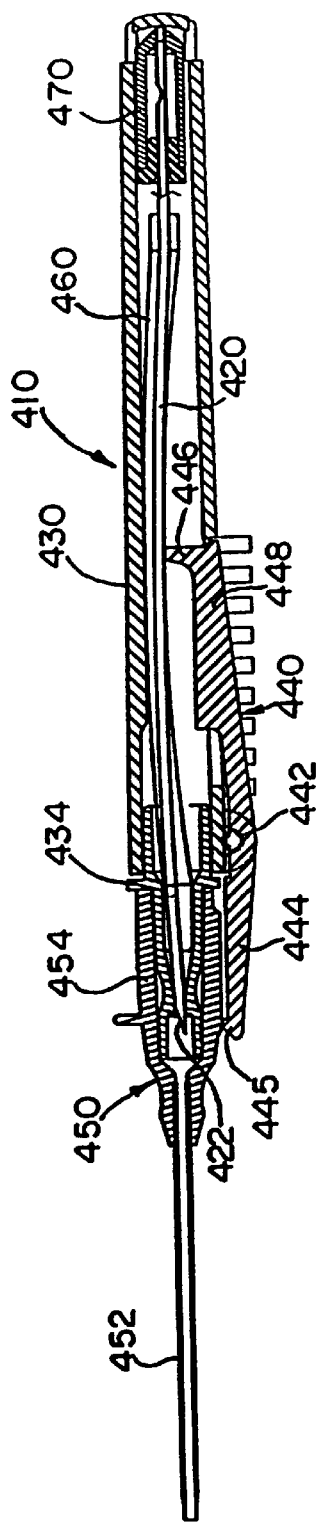

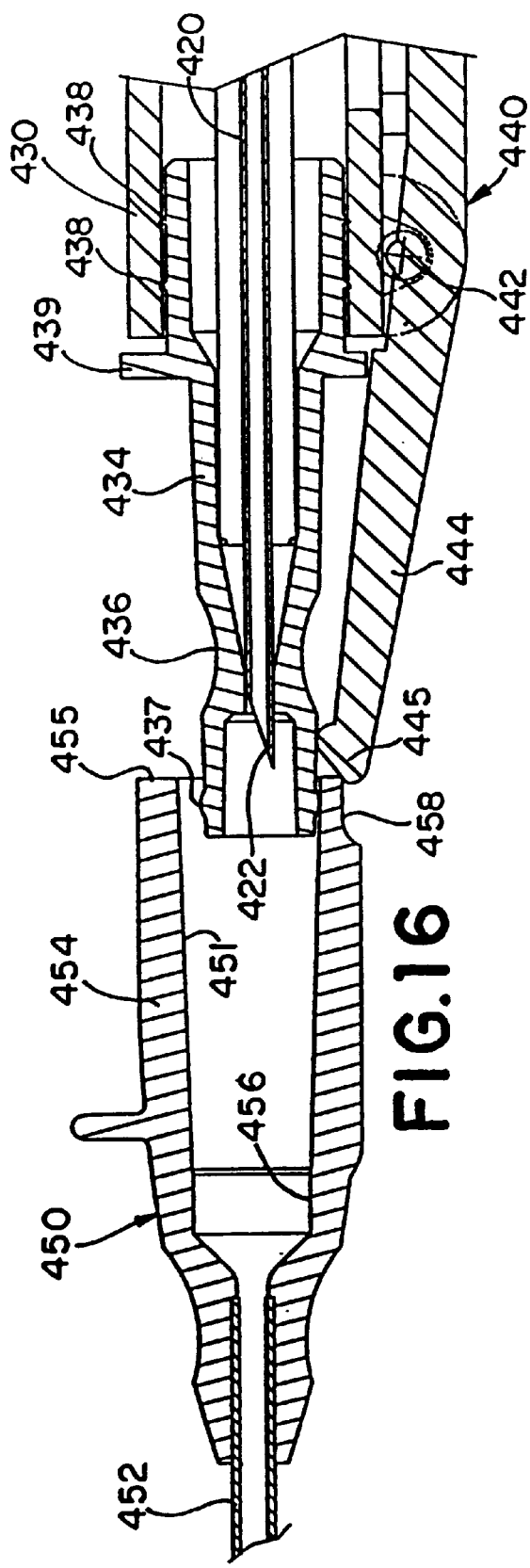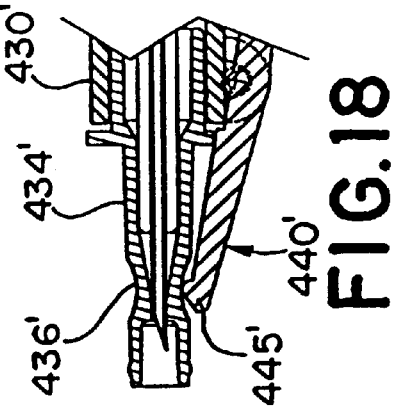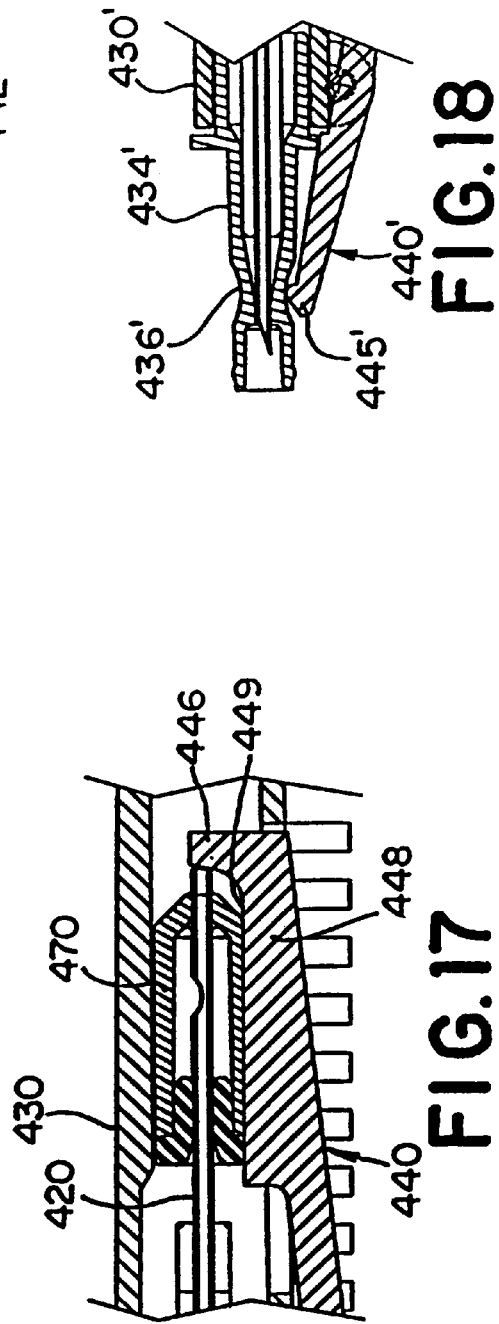

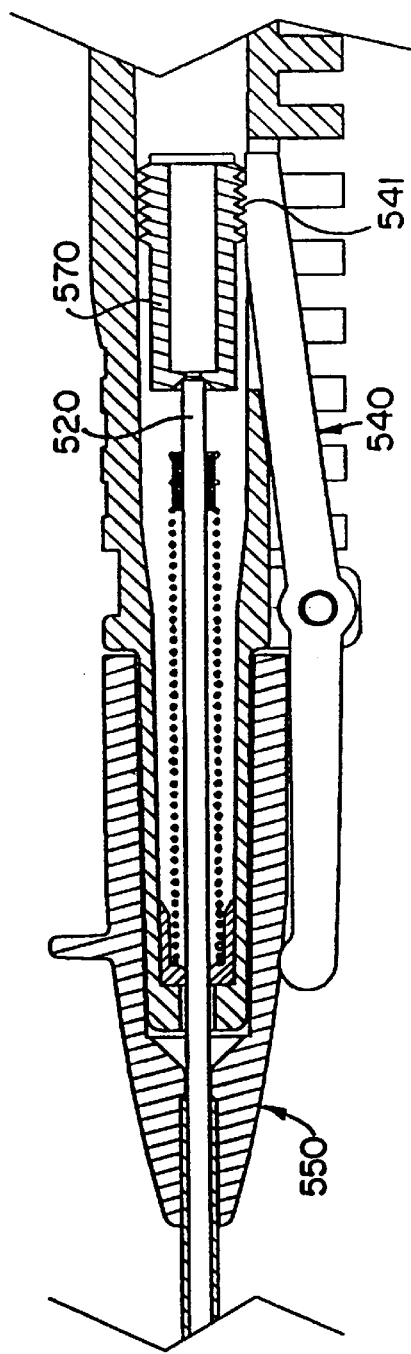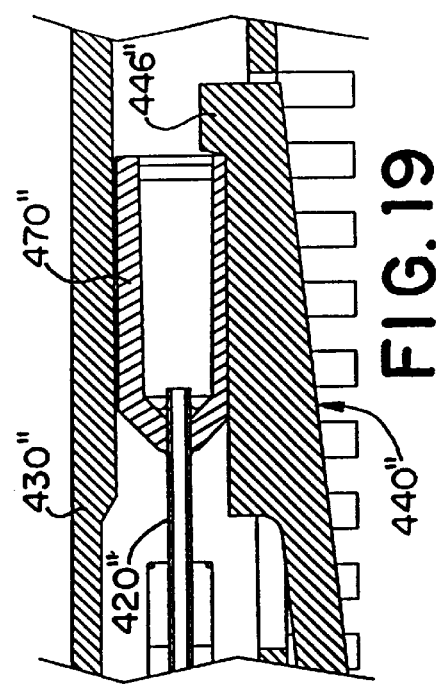

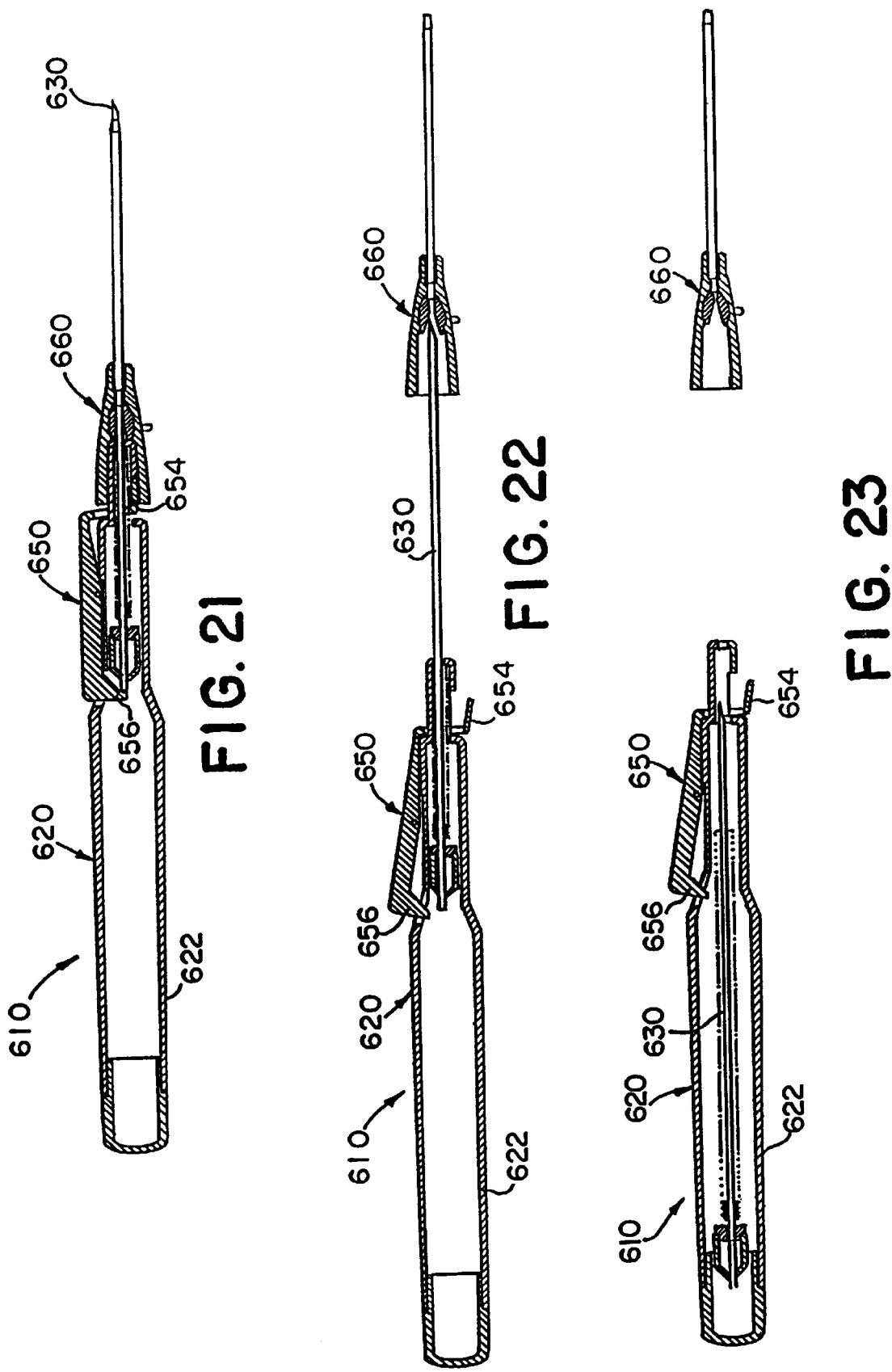

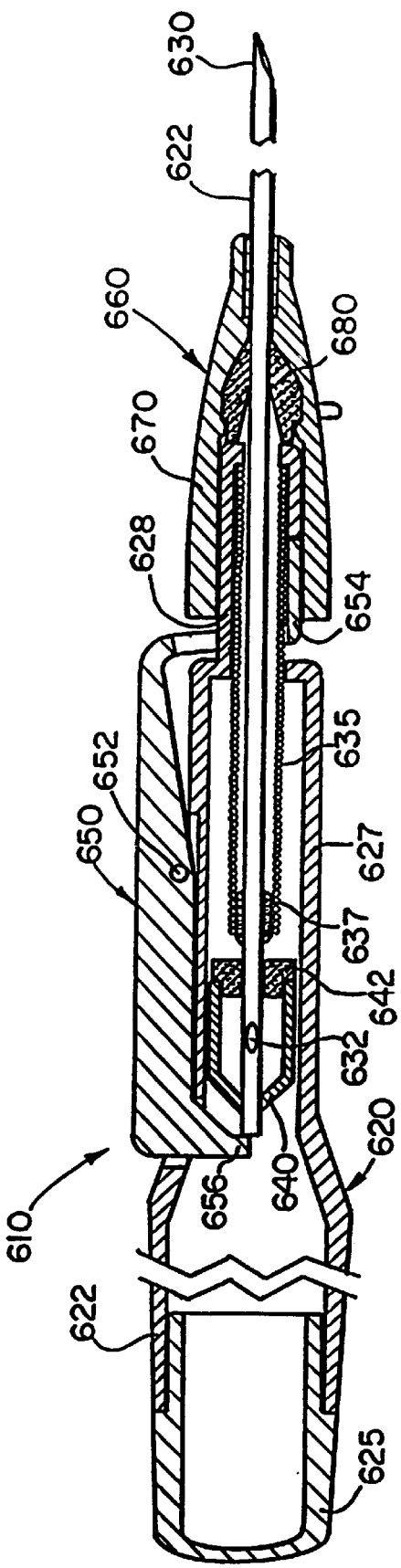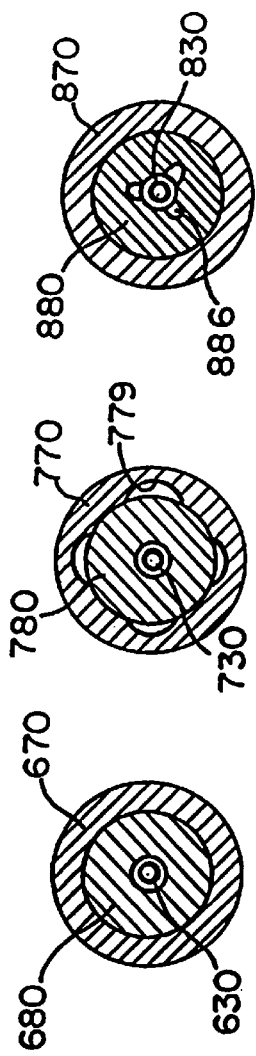

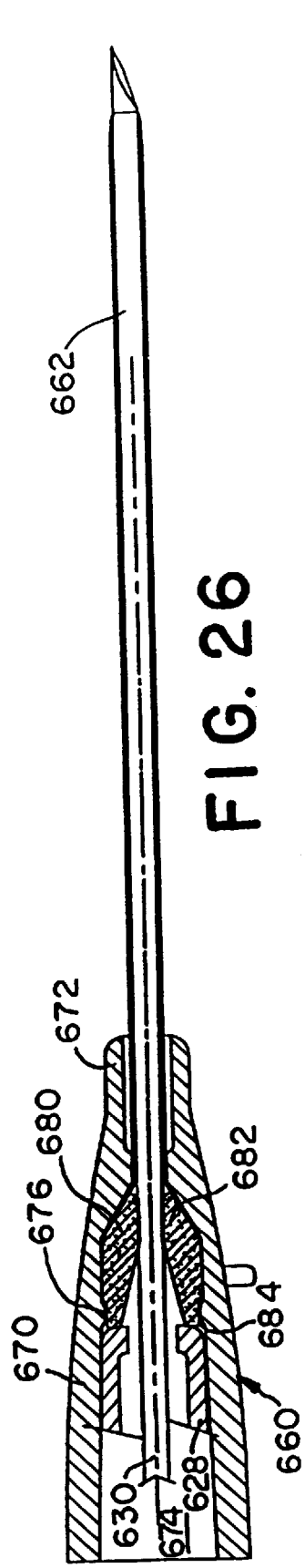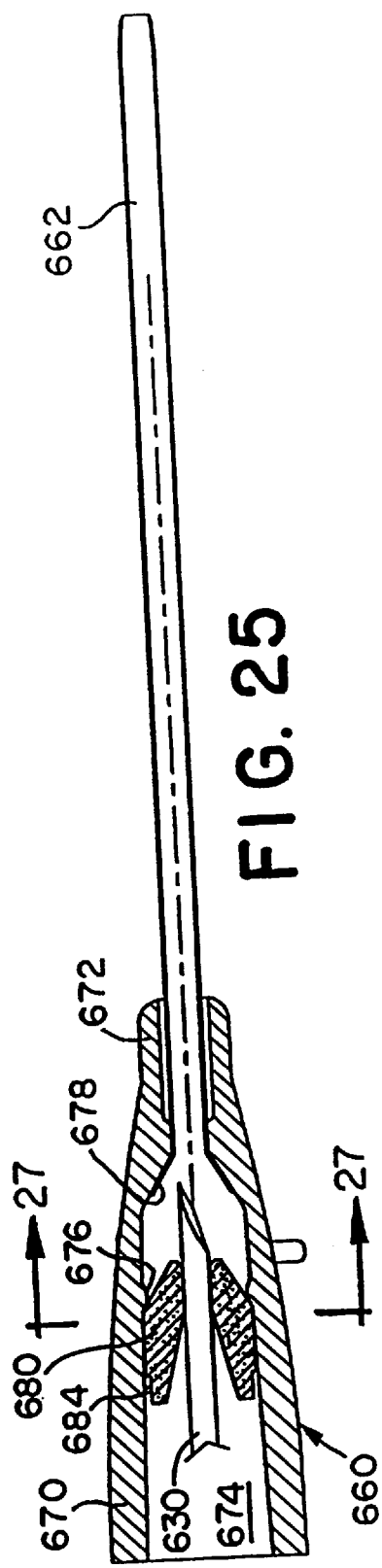

CATHETER INSERTION DEVICE WITH RETRACTABLE NEEDLE

This application claims priority to U.S. Provisional Application No. 60/065,347, filed Nov. 12, 1997.

FIELD OF THE INVENTION

The present invention relates to needle-bearing medical devices used, for example, to insert catheters or guide wires into blood vessels of patients. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is an intravenous catheter insertion device for positioning a needle mounted catheter into a patient's blood vessel. Once the catheter is properly positioned, the catheter insertion device is withdrawn leaving the catheter in place in the blood vessel. Handling of such medical devices after the needle is withdrawn from the patient can result in transmission of various pathogens, most notably human immune virus (HIV), due to an inadvertent needle stick to medical personnel.

Since the mid-1980s, concern over the risk of accidental needle stick injuries has spawned a number of design approaches for safety needle devices. Such devices can be broadly categorized as either sliding sheath needle devices, wherein a physical barrier is positioned over the needle tip after use or as devices with needle retraction, wherein the exposed portion of the needle is retracted into the device after use. The latter category of needle retraction devices can be further subdivided into manual and semi-automatic retraction devices. Manual retraction devices, as exemplified by U.S. Pat. Nos. 4,026,287 to Haller, 4,592,744 to Jagger, 4,808,169 to Haber et al. and 5,067,490 to Haber, require the user to pull or slide a needle-connected mechanism rearwardly to retract the needle into the device. In semi-automatic needle retraction devices, a biasing member, such as a spring, may be employed to push or pull the needle into the device in response to activation by the user of a release mechanism. Such devices are exemplified by U.S. Pat. Nos. 4,813,426 to Haber et al. and 5,125,414 to Dysarz.

U.S. Pat. No. 4,747,831 of Kulli and U.S. Pat. No. 4,900,307 of Kulli show respective catheter insertion devices and syringes with semi-automatic needle retraction. The retraction mechanism shown in the last-mentioned two patents are disclosed to be actuatable by the user upon depression of a release button after the catheter is removed from the insertion device or the needle is removed from the patient.

Of the aforementioned prior art devices which have semi-automatic needle retraction mechanisms, all require a needle structure having an enlarged head or rim extending radially outwardly from the axis of the needle to provide a block or enlarged surface on the needle. The needle is biased toward retraction by a spring which is compressed against the block. Generally, the block, and, hence the needle, is retrained against retraction by a latching arrangement or latch mechanism. In such devices, failure of the latch mechanism or accidental activation would cause inability to retract the needle or premature retraction of the needle occurs. Hence, it would be desirable to provide an automatic needle retraction mechanism in which the latch mechanism operates in a simple fail safe manner.

In addition, the prior art semi-automatic devices require manual actuation by the operator. In many situations, such as an emergency situation, the operator is distracted or rushed so that the manual step necessary to effectuate retraction is not performed, either intentionally or unintentionally. In such instances, the used needle remains exposed, creating a risk of an inadvertent needle stick. Therefore, it would be desirable to provide an automatic needle retraction mechanism in which needle retraction is effectuated by normal operation of inserting the catheter into the patient, without the need to perform a separate manual step.

SUMMARY OF THE INVENTION

With foregoing in mind, the present invention provides a medical device having a hollow housing and a catheter mounted on the housing. The device includes a needle operable between an extended position extending forwardly from the housing and a retracted position in which the needle is enclosed in the housing. A biasing element biases the needle toward the retracted position. A lever mounted on the housing pivots between a locked position and an unlocked position. The lever has a forward portion and a rearward portion. The forward portion engages the catheter thereby preventing the lever from pivoting into the unlocked position. The rearward portion retains the needle against the bias of the biasing element. Upon removal of the catheter from the housing, the catheter disengages the lever thereby allowing the lever to pivot into the unlocked position. The rearward portion then disengages the needle and the biasing element propels the element rearwardly into the housing.

BRIEF DESCRIPTION OF THE DRAWINGS

FIG. 1 is a side sectional view of a catheter insertion device with an insertion needle projecting forwardly into a catheter prior to use;

FIG. 2 is a side sectional view of the catheter insertion device illustrated in FIG. 1, showing the catheter removed and the needle retracted into the device;

FIG. 3 is an enlarged fragmentary sectional view of the device illustrated in FIG. 1;

FIG. 4 is an enlarged fragmentary sectional view of the device illustrated in FIG. 2;

FIG. 5 is a side elevational view of an alternate embodiment of a catheter insertion device with an insertion needle projecting forwardly into a catheter prior to use;

FIG. 6 is a side sectional view of the device illustrated in FIG. 5;

FIG. 7 is a side sectional view of the device illustrated in FIG. 6, with the catheter removed and showing the needle retracted into the device;

FIG. 8 is a sectional view of the device illustrated in FIG. 7, taken along the line 8-8;

FIG. 9 is a side sectional view of another alternate embodiment of a catheter insertion device with an insertion needle projecting forwardly into a catheter prior to use;

FIG. 10 is a side sectional view of the device illustrated in FIG. 9, with the catheter removed and showing the needle retracted into the device;

FIG. 12 is a side sectional view of the preferred embodiment of a catheter insertion device with an insertion needle projecting forwardly into a catheter prior to use;

FIG. 13 is a side sectional view of the catheter insertion device illustrated in FIG. 12, showing the catheter partially removed;

FIG. 14 is a side sectional view of the device illustrated in FIG. 12, with the catheter removed, and showing the insertion needle retracted into the device;

FIG. 15 is a side sectional view of the device illustrated in FIG. 14 with the catheter reattached to the device after the needle has been retracted;

FIG. 16 is an enlarged fragmentary sectional view of the tip of the device illustrated in FIG. 12;

FIG. 17 is an enlarged fragmentary sectional view of the device illustrated in FIG. 12, showing details of the needle retainers;

FIG. 18 is an enlarged fragmentary view of the device illustrated in FIG. 12 having a modified needle retainer;

FIG. 19 is an enlarged fragmentary sectional view of the device illustrated in FIG. 12 having an alternate connection between the needle retainer and the insertion needle;

FIG. 20 is a side sectional view of another alternate embodiment of a catheter insertion device with the insertion needle projecting forwardly into a catheter prior to use;

FIG. 21 is a side view of another alternate embodiment of a catheter insertion device and catheter assembly embodying aspects of the present invention;

FIG. 22 is a side view of the device shown in FIG. 21, shown with the catheter assembly partially removed;

FIG. 23 is a side view of the device shown in FIG. 21, shown with the catheter assembly fully removed;

FIG. 24 is a cross-sectional view of the device shown in FIG. 21;

FIG. 25 is an enlarged cross-sectional view of the catheter assembly shown in FIG. 21, illustrating the catheter assembly before attachment to the catheter insertion device;

FIG. 26 is a cross-sectional view of the device shown in FIG. 25, illustrating the catheter assembly after attachment to the insertion device;

FIG. 27 is a cross-sectional view of the catheter assembly illustrated in FIG. 26 taken along line 27—27;

FIG. 28 is an alternative embodiment of the device illustrated in FIG. 27; and

FIG. 29 is a cross-sectional view of a second alternative embodiment of the device shown in FIG. 27.

DETAILED DESCRIPTION OF THE INVENTION

Figure 11:
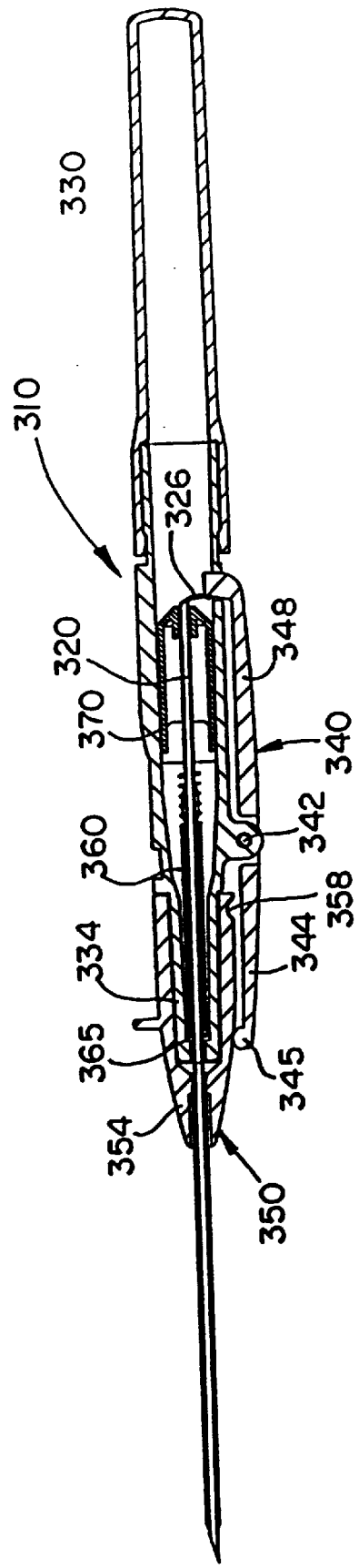
FIG. 11 is a side sectional view of still another alternate embodiment of a catheter insertion device with an insertion needle projecting forwardly into a catheter prior to use.

Referring now to FIGS. 1–4 in general and to FIG. 1 specifically, there is shown a catheter insertion device 10 for inserting a catheter 56 into a patient. The device 10 has a needle 20 to guide the catheter 50 into a vessel of the patient. The insertion device 10 is adapted to automatically retract the needle 20 inside the insertion device 10 when the operator removes the catheter 50 from the device. This automatic retraction feature renders the needle non-reusable and safely disposable.

The catheter insertion device 10 includes a generally cylindrical hollow barrel or housing 30 having a reduced diameter forward tip portion 34. The needle 20 is releasably retained so that the forward end of the needle projects forwardly through a hole in the barrel tip 34. The needle is operable between an extended position and a retracted position. In the retracted position, the needle is enclosed within the housing.

The catheter 50 is initially mounted on the forward end of the catheter insertion device 10 with the needle 20 projecting from the front of the device through the catheter. The catheter 50 comprises a cannula 52 and a hub 54. The cannula 52 sheaths or receives the front portion of needle 20, so that the sharpened point of the needle extends slightly beyond the open end of the cannula.

Referring to FIG. 3, a cylindrical chamber 70 is attached to the needle. The chamber 70 forms a flashback chamber. The flashback chamber 70 is attached near the rear end 26 of the needle 20 so that the flashback chamber encloses a port 24 formed through the side of the needle 20. The rearward end of the needle 20 is preferably plugged so that fluid flowing through the needle flows through the side port 24 and into the flashback chamber 70. In the present instance, an adhesive plug such as epoxy is used to plug the rearward end of the needle. The forward end of the flashback chamber is closed by a porous vent plug 72. The vent plug 72 allows the passage of air out of the chamber 70, while preventing blood from escaping from the flashback chamber 70.

The needle 20 is biased rearwardly toward its retracted position by a biasing element 60. In the present instance, the biasing element is a spring 60 that surrounds the needle. The spring 60 is connected to the needle preferably by an adhesive, such as epoxy 62. The needle is releasably retained against the bias of the spring 60 by a needle retainer or lever arm 40 that is pivotally connected to the housing 30.

The needle retainer 40 has a forward portion 44 and a rearward portion 48. In the present instance, the forward portion 44 extends in the forward direction from a pivot 42, and the rearward portion 48 extends rearwardly from the pivot 42. The interior surface of the forward portion 44 of the retainer 40 abuts with the hub 54 of the catheter 50 when the catheter is mounted on the insertion device 10. Preferably, the forward portion 44 of the retainer 40 abuts or engages the external surface of the catheter hub 54. Alternatively, the forward portion may engage the internal surface of the catheter hub 54. The rearward portion 48 of the needle retainer 40 is located rearwardly from the pivot point and catheter 50, when the catheter is mounted on the insertion device.

The rearward portion 48 of the needle retainer 40 functions as a release lever 41 having a latch 46 formed thereon. The lever 41 is pivotable between a locked position and an unlocked position. In the locked position, the release lever 41 extends generally parallel to the longitudinal axis of the device 10. The latch 46, on the end of the release lever 41, passes through an opening 32 in the side of the barrel 30, so that the rear end 26 of the needle 20 abuts the latch to retain the needle in its extended position.

The engagement between the forward portion 44 and the catheter hub 54 prevents the release lever 41 from pivoting to its unlocked position when the catheter is mounted on the insertion device. The rear portion 48 of the retainer 40 is preferably biased to pivot away from the side of the housing 30. After the catheter 50 is removed past the end of the lever 44, the retainer is free to pivot into its unlocked position, thus moving the latch 46 out of engagement with the rear end of the needle 20. The spring 60 then propels the needle rearwardly into the housing 30 to the position shown in FIGS. 2 and 4.

The catheter insertion device is initially provided in the configuration shown in FIG. 1. The operator of the catheter insertion device 10 first uses the needle point 22 to pierce a blood vessel of the patient. When the needle point 22 pierces the patient's blood vessel, blood flows through the needle 20 and through the port 24 of the needle. The blood emerges from the port 24 near the back end 26 of the needle 20 and collects in the transparent flashback chamber 70. The appearance of blood in the flashback chamber 70 serves as a visible indication to the operator that a blood vessel has been appropriately pierced, and that the catheter 50 is properly positioned. The operator then slides the catheter hub 54 off of the forward end of the device 10, in the direction of the pointed end 22 of the needle 20, to insert the catheter lumen 52 into the patient's blood vessel. This motion of removing the catheter hub 54 from the device causes the retainer 40 to automatically pivot out of contact with the end of the needle when the rim 55 of the catheter hub passes the end of lever 44. The needle is thereby released and withdrawn into the barrel 30 of the catheter insertion device 10 under the bias of spring 60. The operator need not perform any additional action to effectuate retraction of the needle other than that required by a normal catheter insertion procedure. The configuration of the used catheter insertion device 10 with the needle 20 retracted, is shown in FIG. 2. Thus, the needle is automatically retracted into the insertion device as the catheter is removed from the device in the usual manner.

Referring now to FIGS. 5–8, there is shown an alternate embodiment of a catheter insertion device 110. The alternate embodiment shown in FIGS. 5–8 incorporates elements that are similar to elements in the first embodiment described above in connection with FIGS. 1–4. Parts in FIGS. 5–8 that are similar to the parts in FIG. 1 are numbered by the same number designator with the addition of 100's thereto.

The catheter insertion device 110 includes an insertion needle 120 projecting forwardly from a barrel or housing 130. A cup-shaped sealing member 165 is positioned in the forward end or tip 134 of the housing 130 to provide a fluid-tight seal between the needle 120 and the housing. The needle 120 is releasably retained by a needle retainer 140 comprising a release lever 141. The needle retainer 140 engages a catheter 150 mounted on the tip 134 of the housing 130. In this manner, the catheter 150 impedes pivoting of the needle retainer 140 and prevents retraction of the needle 120 while the catheter is mounted on the housing 130 of the device 110.

The needle retainer 140 includes a forward portion 144 and a rearward portion 148. The forward portion 144 is forward of the pivot 142, and the rearward portion 148 is rearward of the pivot. In the embodiment of FIG. 5, the needle retainer is angled so that the forward portion 144 extends at an angle relative to the rearward portion 148. More specifically, the lever 140 forms an oblique angle about the pivot point so that the rear portion 148 is inclined or slanted into the housing 130 toward its latch end 146.

The housing 130 includes a gripping area that includes a plurality of longitudinally spaced ridges 166 projecting from the exterior surface of the housing 130. The housing 130 further includes a slot 167 formed along the gripping portion. The rearward portion 148 of the needle retainer 140 extends along the slot 167 and into the interior of the housing 130 as shown in FIG. 6. The arrangement of the slot 167 and the ridges 166 provide a guard to prevent the operator from contacting the rearward portion 148 of the needle retainer 140 during use of the device. In this manner, the operator is prevented from manually interfering with normal operation or separately controlling operation of the needle retainer 140.

The forward portion 144 of the needle retainer 140 includes an enlarged portion 145 that contacts the catheter hub 154 when the catheter 150 is mounted on the device, as shown in FIGS. 5 and 6. As shown in FIG. 8, the protrusion 145 is contoured to cooperate with the external surface of the tip 134 of the housing. In this arrangement, as shown in FIG. 7, when the catheter is removed, the protrusion 145 overlaps the tip, thereby increasing the distance that the needle retainer 140 is facilitated to pivot.

As in the embodiment described above in connection with FIGS. 1–4, the catheter insertion device 110 in FIG. 5 is also operable to automatically retract the needle without manual intervention or requiring a separate step for retraction. The needle retainer 140 is biased toward an unlatched position, so that when the catheter 150 is removed from the insertion device 110, the needle retainer 140 automatically pivots into its unlatched position, releasing the needle 120. The spring 160 then propels the needle 120 rearwardly into the housing 130, so that the sharpened tip of the needle 120 is safely enclosed within the housing.

Referring to FIGS. 6 and 7, the tip 134 of the device and the needle retainer 140 are configured so that the forward end of the release lever 141 is rearward of the forward end of the tip. When the needle retainer 140 disengages the catheter hub 154, the catheter still overlaps the tip 134. In this way, the needle remains enclosed by the catheter 150 and the barrel 130 during and after retraction.

After the catheter has been inserted into the patient and the needle 120 has been retracted, the tip 134 of the device can be inserted into the catheter 150 to replug the catheter to prevent blood from leaking out of the catheter. For this reason, the catheter 150 and/or the forward end of the needle retainer 140 are configured to facilitate pivoting of the needle retainer so that the forward end of the needle retainer does not interfere with replugging of the catheter. Specifically, the forward edge of the enlarged portion 145 is rounded so that the forward portion 144 of the needle retainer 140 pivots downwardly from the perspective of FIG. 7 when the enlarged portion engages the rim 155 of the catheter 150. Alternatively, the rim 155 can be rounded or tapered, or the enlarged portion 145 can be tapered to facilitate pivoting of the needle retainer 140 upon forward axial displacement of the tip 134 relative to the catheter 150 after the catheter has been removed from the device a sufficient amount to disengage the needle retainer.

Referring now to FIGS. 9–10, there is shown another alternative embodiment of a catheter insertion device 10 of FIG. 1. The device 210 incorporates elements that are similar to ones previously described. Such elements are designated with the same number designations with the addition of 200's thereto.

The catheter insertion device 210 includes an insertion needle 220 projecting forwardly from a barrel or housing 230. A cup-shaped seal member 265 is positioned in the forward end or tip 234 of the housing 230 to provide a fluid-tight seal between the needle 220 and the housing 230. The needle 220 is releasably retained by a pivotable needle retainer 240 comprising a release lever. One end of the needle retainer 240 engages a catheter 250 mounted on the tip 234 of the housing 230. In this arrangement, the catheter 250 impedes the needle retainer 240 from releasing the needle 220 while the catheter is mounted on the housing 230 under the retainer 240.

More specifically, the needle retainer 240 includes a forward portion 244 and a rearward portion 248. The forward portion 244 extends in the forward direction from a pivot point 242, and the rearward portion 248 extends rearwardly from the pivot 242. The housing includes a shroud 268 that encloses the rearward portion 248 of the needle retainer 240. The shroud 268 operates as a guard to prevent the operator from contacting the rearward portion 248 of the needle retainer 240 during use of the device. In this arrangement, the shroud 268 prevents the operator from manually preventing or controlling operation of the needle retainer 240 that automatically releases the needle for retraction, when the catheter is moved free of the forward portion 244 of the retainer 240.

In the embodiment in FIGS. 9 and 10, the rearward end 226 of the needle 220 is preferably bent transverse to the longitudinal axis of the needle. A latch 246 that is integral with the rearward portion 248 of the needle retainer projects into the interior of the housing 230. The latch 246 includes a groove 269 that engages the bent end 226 of the needle. Preferably the bent end 226 is bent at a predetermined orientation to the bevel angle of the needle tip. In this manner, the groove 269 in the latch 246 cooperates with the bent end 226 to maintain the bevel of the needle tip in a selected circumferential orientation when the needle is in the extended position.

Referring now to FIG. 11, there is shown yet another alternate embodiment of a catheter insertion device 310. Elements of the device 310 that are similar to the corresponding elements of the embodiments discussed above are designated with the same reference numbers with the addition of 300's thereto.

The catheter insertion device 310 includes an insertion needle 320 projecting forwardly from a barrel or housing 330. A cup-shaped seal member 365 in the forward end or tip 334 of the housing 330 provides a fluid-tight seal between the needle 320 and the housing 330. The needle 320 is releasably retained by a needle retainer 340 comprising a release lever. The needle retainer 340 engages a catheter 350 mounted on the tip 334 of the housing 330. In this arrangement, the catheter 350 impedes the needle retainer 330 from releasing the needle 320 while the catheter is mounted on the housing 330.

The device 310 includes a needle retainer 340 having a forward portion 344 extending forwardly from a pivot 342, and a rearward portion 348 extending rearwardly from the pivot 342. As shown in FIG. 11, the forward and rearward portions of the retainer 340 are integrally formed.

The forward portion 344 includes a protuberance or detent 345 that cooperates with the catheter 350. More specifically, the catheter 350 includes a groove or recess 358 formed in the catheter hub 354 that cooperates with the detent 345 at the forward end of the needle retainer 340. When the catheter is mounted on the housing prior to use, the detent 345 is positioned forward of the recess 358. When the catheter is moved off of the device until the hub 354 is substantially, but not completely clear of the housing, the detent 345 engages the recess 358. The detent 345 and the recess 358 are configured to cooperate to produce a visual, audible and/or tactile signal for the operator when the detent engages the recess. In this arrangement, the recess 358 operates with the needle retainer 340 as a sensor for indicating to the operator that the catheter is about to be removed from the insertion device 310. After the signal from the sensor, continued forward displacement of the catheter 350 completely removes the catheter from the insertion device, causing retraction of the needle 320 into the housing. Hence, the signal produced between the detent 345 and recess 358 provides the operator with knowledge that continued removal of the catheter will cause retraction of the needle.

Referring now to FIGS. 12–18, yet another embodiment is illustrated. The embodiment in FIGS. 12–18 is the preferred embodiment and it operates similarly to the embodiments illustrated in FIGS. 1–11. Elements of the device 410 that are similar to the corresponding elements of the embodiments discussed above are designated with the same reference numbers with the addition of 400's thereto.

The preferred embodiment includes numerous advantageous features, such as the ability to adjust the length of needle that projects from the forward end of the catheter, the ability to align the bevel of the needle relative to the housing, an indicator for providing a audible, visual or tactile signal to the operator that continued forward removal of the catheter will cause retraction, and the ability to seal the catheter after needle retraction to reduce or eliminate blood leakage from the catheter after the catheter is inserted into the patient. The preferred embodiment also includes the feature of enclosing the needle during and after retraction of the needle so that the needle is not exposed after being inserted into the patient.

Referring now to FIGS. 12 and 16, the device 410 includes a barrel 430, a catheter 450 releasably mounted on the barrel, an insertion needle 420, and a needle retainer 440 releasably retaining the needle projecting forwardly from the barrel. The needle retainer 440 cooperates with the catheter, such that removing the catheter from the barrel 430 causes the needle retainer to disengage the needle. A spring 460 attached to the needle 420 then propels the needle rearwardly into the barrel 430.

The needle retainer 440 operates similarly to the needle retainer described above in connection with the previously described embodiments. The needle retainer pivots 440 about a pivot point 442, pivoting between a latched position and an unlatched position. In the latched position, the forward end of the needle retainer 440 engages the catheter 450, and a latch 446 at the rearward end of the needle retainer engages the needle 420. In this way, in the latched position, the needle retainer 440 retains the needle in an extended position against the bias of the spring 460, so that the pointed end 422 of the needle projects beyond the forward end of the catheter 450. When the catheter 450 is removed from the barrel 420, the needle retainer 440 pivots into the unlatched position. In the unlatched position, the needle retainer latch 446 disengages the needle 420 and the spring propels the needle rearwardly into the barrel 430.

The needle retainer 440 includes an elongated arm having a forward portion 444 extending forwardly of the pivot 442 and a rearward portion 448 extending rearwardly from the pivot. Referring to FIG. 17, the latch 446 is formed at the rearward end of the needle retainer 440. The latch 446 engages the rearward end of the needle 420 to releasably retain the needle.

The forward portion 444 of the needle retainer includes a detent 445 that cooperates with the catheter 450. More specifically, the catheter 450 includes a groove or recess 458 formed in the catheter hub 454 that cooperates with the detent 445 at the forward end of the needle retainer 440. When the catheter is mounted on the housing prior to use, the detent 445 is positioned forward of the recess 458.

When the catheter is moved off of the device until the hub 454 is substantially, but not completely clear of the housing, the detent 445 engages the recess 458. The detent 445 and the recess 458 are configured to cooperate to produce a visual, audible and/or tactile signal for the operator when the detent engages the recess. In this arrangement, the recess 458 operates with the needle retainer 440 as a sensor for indicating to the operator that the catheter is about to be removed from the insertion device 410. After the signal from the sensor, continued forward displacement of the catheter 450 completely removes the catheter from the insertion device, which actuates retraction of the needle 420 into the housing. Hence, the signal produced between the detent 445 and recess 458 provides the operator with knowledge that continued removal of the catheter will cause retraction of the needle.

The catheter 450 includes a flexible, elongated cannula 452 attached to the catheter hub 454. The cannula 452 telescopingly engages the needle so that the cannula sheaths the needle, with the sharpened tip of the needle 422 projecting beyond the forward end of the cannula. The rearward edge of the sharpened tip 422 is referred to as the heel of the needle bevel. The length of the needle between the heel of the needle bevel and the forward end of the cannula is referred to as the lie length. Preferably, the lie length is adjustable.

In the present instance, the lie length is adjustable by maintaining the extended position of the needle constant, and adjusting the position of the catheter 450 when the catheter is mounted on the barrel prior to use. The tip of the barrel 420 is adjustable to provide for adjustment of the catheter.

Referring now to FIG. 16, the barrel 420 includes a displaceable tip 434. In the present instance, the tip 434 is a separate component that is inserted into an opening at the forward end of the barrel 430. The tip 434 includes an external circumferential flange 439 against which the rearward edge 455 of the catheter hub 454 seats. Therefore, varying the axial position of the tip 434 adjusts the axial position of the flange 439 thereby adjusting the lie length.

The tip 434 includes a generally cylindrical rearward portion having an external diameter that is slightly less than the internal diameter of the forward portion of the barrel 430. A plurality of barbs 438 project from the external surface of rearward end of the tip 434. The barbs 430 engage the internal surface of the barrel 430 to connect the tip 434 to the barrel. The axial position of the flange 439 is determined by the distance that the rearward end of the tip is inserted into barrel 430. By adjusting the amount the tip is inserted, the axial position of the flange 439 is adjusted, thereby adjusting the lie length.

Referring to FIGS. 12–16, the tip 434 of the device and the needle retainer 440 are configured so that the forward end of the release lever is rearward of the forward end of the tip. When the needle retainer 440 disengages the catheter hub 454, the catheter still overlaps the tip 434. In this way, the needle remains enclosed by the catheter 450 and the barrel 430 during and after retraction.

Referring to FIG. 16, the tip 434 further includes a constricted portion 435 having an internal diameter slightly larger than the external diameter of the needle 420. The close fit between the constricted portion 435 and the needle limits leakage of blood into the barrel 430 during a replugging step, as described further below. In addition, an external circumferential rib 437 protrudes radially from the front end of the tip 434. The rib 437 cooperates with the internal cavity 451 of the catheter hub 454 to provide a fluid-tight seal. The internal cavity 451 is tapered, having a major diameter that is greater than the diameter of the rib 437 on the tip 434. Preferably, a substantially cylindrical zero draft zone 456 is formed at the forward-most portion of the internal cavity 451. The zero draft zone 456 has an internal diameter that is similar to the external diameter of the rib 437 on the tip 434. In this way, when the catheter 450 is mounted on the barrel 430, the rib 437 engages the zero draft zone 456 to form a fluid-tight seal.

Referring to FIG. 15, after the catheter has been inserted into the patient and the needle 420 has been retracted, the tip 434 of the device can be inserted into the catheter 450 to replug the catheter to prevent blood from leaking out of the catheter. For this reason, the catheter 450 and/or the forward end of the needle retainer 440 are configured to facilitate pivoting of the needle retainer so that the forward end of the needle retainer does not interfere with replugging of the catheter. Specifically, the forward edge of the enlarged portion 445 is tapered so that the forward portion 444 of the needle retainer 440 pivots downwardly from the perspective of FIGS. 14 and 15 when the enlarged portion engages the rim 455 of the catheter 450. Alternatively, the rim 455 can be rounded or tapered to facilitate pivoting of the needle retainer 440 upon forward axial displacement of the tip 434 relative to the catheter 450 after the catheter has been removed from the device a sufficient amount to disengage the needle retainer from the needle 420.

Referring to FIGS. 15–17, the catheter 450 is replugged after retraction by inserting the tip 434 of the barrel 430 into the catheter cavity 451 so that the circumferential rib 437 engages the zero draft zone 456. The rib 437 and the zero draft zone 456 cooperate to form a fluid-tight seal so that blood does not leak from the catheter around the tip 434. In addition, the retracted needle 420 forms a seal with the constricted portion 435 of the tip 434 to reduce or eliminate blood leakage from the catheter 450 into the barrel 430. In the retracted position, the latch 446 deflects and/or deforms the needle as shown in FIG. 15.

It is desirable to align the sharpened tip 422 of the needle 420 so that the bevel of the sharpened tip is circumferentially located relative to the barrel 430, as illustrated in FIG. 12. Specifically, preferably, the sharpened tip is circumferentially located so that the forward-most point of the sharpened tip is vertically positioned below the heel of the tip bevel. In the present instance, the flashback chamber 470 is configured to cooperate with the ledge 449 of the needle retainer to facilitate aligning the bevel of the needle, as described below.

The flashback chamber 470 is generally cylindrical, and includes a flat surface extending along the length of the flashback chamber. The desired circumferential orientation of the needle bevel is located relative to the flat on the flashback chamber when the flashback chamber is connected to the needle. Referring to FIG. 17, the rearward portion 448 of the needle includes a generally planar surface or ledge 449 that cooperates with the flashback chamber 470 to circumferentially align the needle 420 relative to the barrel 430. As shown in FIGS. 12 and 17, when the needle retainer 440 is disposed in the latched position, the flat on the flashback chamber 470 is aligned with and engages the ledge 449 of the needle retainer. In this way, the flashback chamber 470 and the attached needle 420 are circumferentially located relative to the needle retainer, and in turn to the barrel 430.

The tip 434 further includes an external circumferential depression or recess 436. Initially, the catheter 450 encloses the tip 434 so that the operator cannot see the recess 436. As the operator removes the catheter 450 from the tip 434, the recess 436 is uncovered so that the operator can see the recess. After the recess 436 is uncovered, continued removal of the catheter 450 displaces the catheter beyond the enlarged forward end 445 of the needle retainer 440, so that the needle retainer pivots into the unlatched position, as shown in FIG. 16. In this way, the recess operates as a visual indicator to the operator, providing a visual signal that continued forward displacement of the catheter will cause needle retraction. Preferably, the recess 436 is textured to enhance the visual distinction between the recess and the rest of the external surface of the tip. Alternatively, a different visual indicator can be provided, such as a circumferential colored line located on the tip 434 axially rearwardly of the enlarged forward end 445 of the needle retainer 440.

Referring now to FIGS. 18–20, several design alternatives are shown that can be incorporated into one or more of the embodiments described above. For instance, in FIG. 18, recess 436' is shown axially aligned with the enlarged forward end 445' of the needle retainer 440'. In this alternative configuration, the recess 430' cooperates with the needle retainer to extend the pivot range of the needle retainer. The increased pivot range facilitates pivoting the latch 446' of the needle retainer radially outwardly beyond the flashback chamber 470' attached to the needle 420'.

FIG. 19 illustrates an alternate manner for connecting the needle and the needle retainer. In the previously described embodiments, the needle retainer engages the rearward end of the needle. In FIG. 19 the latch 446" of the needle retainer 440" engages the flashback chamber 470", which is connected to the rearward end of the needle 420". In such a configuration, the needle 420" need not include a side port. Instead, the rearward end of the needle communicates with an opening at the forward end of the flashback chamber.

FIG. 20 illustrates yet another alternative for retaining the needle. In FIG. 20, the needle retainer latch includes a plurality of serrated teeth 546. The serrated teeth 546 on the needle retainer 540 cooperate with a mating set of serrated teeth formed on the exterior of the flashback chamber 570. The flashback chamber 570 abuts the rearward end of the needle 520, so that the needle is retained in an extended position when the needle retainer 540 engages the flashback chamber. In the present instance, the flashback chamber is not attached to the needle 520, so that the flashback chamber dissociates from the needle after the needle is retracted. The mating serrations also provide a mechanism for adjusting the needle relative to the catheter 550 during assembly, for adjusting the needle lie.

Referring now to drawings 21–27 in general, and FIGS. 21–23 specifically, yet another embodiment of a catheter insertion device 610 and catheter assembly 660 are illustrated. The insertion device 610 includes an insertion needle 630 over which the catheter assembly 660 is telescopingly engaged. Inserting the needle 630 into a patient also inserts the catheter assembly 660 into the patient. Once the catheter assembly 660 is inserted into the patient, the insertion needle 630 is withdrawn from the patient, leaving the catheter assembly inserted in the patient. After the insertion needle 630 is withdrawn from the catheter assembly 660, the insertion needle is retracted into the housing of the insertion device 610.

Referring now to FIG. 24, the details of the catheter insertion device 610 and catheter assembly 660 are illustrated. The catheter insertion device 610 includes a hollow housing 620 having a generally cylindrical barrel 622. The rearward end of the barrel 622 is generally open. An end cap 625 is inserted into the open end of the barrel and fixedly connected to the barrel to seal the rearward end of the barrel 622. The forward end of the barrel 622 has a reduced diameter gripping portion 627 for manipulating the device during use. A reduced diameter cylindrical nose portion 628 projects forwardly from the gripping portion 627. The nose 628 includes a front opening through which the insertion needle 630 extends.

A spring 635 is disposed around the needle 630 within the housing 620. The spring is attached to the needle by an adhesive 637, such as epoxy. The spring 635 bears against the forward-most interior surface of the nose 628, biasing the needle 630 rearwardly.

The device includes a flashback chamber 640 for indicating whether the insertion needle 630 has pierced a vein when the catheter assembly is inserted into a patient. The flashback chamber 640 is a generally cylindrical chamber disposed about the needle 630 within the housing 620. The flashback chamber 640 is attached to the needle 630 so that the chamber encloses a side port 632 in the side of the insertion needle 630. The rearward end of the flashback chamber 640 is closed, forming a seal with the side of the insertion needle 630. The forward end of the flashback chamber 640 is generally open. A hydrophobic vent plug 642 inserted into the forward end of the flashback chamber seals the forward end of the chamber. In this way, when the insertion needle 630 punctures a vein in the patient, blood flows into the needle. The rearward end of the needle is closed so that the blood flows through the side port 632 into the flashback chamber 640. The vent plug 642 prevents the blood from leaking into the interior of the housing 620. The flashback chamber 640 and the housing 620 are made from transparent or translucent materials so that an operator can detect the presence of blood in the flashback chamber.

A safety lever 650 pivotally mounted on the housing 620 engages the needle 630 to prevent the needle from being retracted into the housing while the catheter assembly 660 is mounted on the housing. The safety lever is axially elongated and is pivotally mounted on a pivot pin 652 so that the lever extends along the length of the gripping portion 627 of the housing. The safety lever 650 includes an integral needle latch 656 that projects transversely into the interior of the housing 620. The needle latch 656 has a shoulder that abuts the rear end of the insertion needle 630. The forward end of the safety lever 650 includes an integral catheter latch 654 that extends through the nose 628 of the housing and into the interior of the catheter assembly 660.

The safety lever 650 pivots between a latched position and an unlatched position. In the latched position, the needle latch 656 engages the rearward end of the needle 630 as illustrated in FIG. 24. In the unlatched position, the needle latch 656 is pivoted out of engagement with the insertion needle 630, as illustrated in FIG. 22. In the unlatched position the needle is released so that the spring 635 propels the needle 630 rearwardly into the housing 620. When the catheter assembly 660 is inserted onto the nose 628 of the insertion device 610, the catheter latch 654 bears against the interior of the catheter assembly 660, so that the safety lever 650 cannot be pivoted into the unlatched position. Once the catheter assembly 660 is detached from the insertion device 610, the safety lever 650 can be pivoted into the unlatched position.

The safety lever is mounted on the gripping portion 627 so that the safety lever can be readily depressed by the operator to pivot the lever into the unlatched position. In addition, preferably a biasing member, such as a spring, bears against the safety lever 650, biasing the safety lever into the unlatched position. Alternatively, the safety lever can be configured so that the safety lever automatically pivots into the unlatched position after the catheter assembly 660 is removed from the insertion device 610.

In addition to the safety lever 650 that retains the needle, preferably the needle is also retained by a frictional element in the catheter assembly 660. Referring now to FIG. 25, the details of the catheter assembly 660 can best be seen. The catheter assembly 660 includes a flexible catheter 662 fixedly mounted to a catheter hub 670. The catheter hub 670 is generally hollow having a cavity 674 that opens to the rearward end of the hub. The catheter hub 670 is generally frustoconical, convergingly tapering to a reduced diameter cylindrical tip 672 at the forward end of the hub. The tip 672 has a cylindrical bore that is in fluid communication with the rearward cavity 674 of the hub. The flexible catheter 662 projects forwardly from the tip 672 of the catheter hub and extends through the cylindrical bore of the tip into the rearward cavity 674.

The forward portion of the rear cavity 674 convergingly tapers into the cylindrical bore of the tip 672, forming a tapered seat 678. An annular rim 676 protrudes into the cavity 674 to define the rearward end of the tapered seat 678.

Referring now to FIGS. 25 and 26, a frictional element 680 is disposed within the tapered seat 678. The forward end of the frictional element 680 is generally frustoconical having a taper that corresponds to the tapered seat 678. The rearward portion of the frictional element 680 has a cavity that is larger in diameter than the needle. The forward frustoconical portion of the frictional element 680 is a gripping portion 682 that has a bore that is similar to the diameter of the needle 630. The frictional element 680 is made of a flexible resilient material so that the bore of the gripping portion 682 can expand and contract. Preferably, in its relaxed state, the bore of the gripping portion 682 is greater than the needle so that the needle can readily pass through the gripping portion.

Before the catheter assembly 660 is attached to the catheter insertion device 610, preferably the frictional element 680 is disposed in the catheter cavity 674 rearward of the tapered seat 678, as shown in FIG. 25. The catheter assembly 660 is then connected to the insertion device 610 by sliding the catheter assembly over the insertion needle 630. The interior walls of the cavity 674 do not substantially compress the gripping portion, so that the needle readily slides through the catheter assembly 660. When the catheter hub 670 engages the nose 628 of the insertion device, the nose forces the frictional element 680 into the tapered seat 678, wedging the frictional element 680 against the front tapered wall of the tapered seat. When the frictional element 680 is wedged into the tapered seat 678, the frictional element is compressed so that the gripping portion 682 constricts to frictionally engage the insertion needle 630 thereby retaining the needle and forming a fluid-tight seal with the needle. The rearward end of the frictional element 680 has a circumferential groove 684 that cooperates with the annular rib 676 in the cavity 674 to prevent the frictional element from being displaced rearwardly when the needle 630 is detached from the catheter assembly 660.

Configured in this way, the device operates as follows. As shown in FIG. 21, initially the catheter assembly 660 is mounted on the end of the insertion device 610 so that the safety lever 650 is in the latched position. The needle extends through the catheter assembly 660 so that the sharpened tip of the needle projects forwardly from the catheter 662, as shown in FIG. 26. The insertion needle 630 and catheter 662 are then inserted into a patient. When the operator notices blood in the flashback chamber 640, the operator withdraws the needle from the catheter assembly 660 to remove the catheter assembly from the insertion device 610. After the catheter assembly is removed from engagement with the catheter latch 654 on the housing nose 628, the safety lever 650 pivots into the unlatched position. In the unlatched position, the needle latch 656 does not retain the needle from retracting. However, the gripping portion 682 of the frictional element 680 in the catheter assembly frictionally retains the insertion needle 630 to prevent the needle from retracting. After the needle 630 is withdrawn from the catheter assembly 660, the spring 635 propels the needle 630 rearwardly into the housing 620 so that the needle is completely enclosed within the housing. In this way, to affect retraction, the length of the needle is withdrawn from the catheter assembly 660 until the gripping portion 682 releases the needle.

After the catheter assembly 660 is inserted into the patient and the insertion device is removed from the catheter assembly, fluid medication can be administered to the patient intravenously through the catheter. The gripping portion 682 of the frictional element 680 may limit the fluid flow through the catheter assembly 660. Therefore, as shown in FIG. 28, longitudinal grooves 779 may be formed in the interior of the catheter hub 770. The grooves 779 provide fluid paths for fluid flow between the rear cavity 774 and the catheter 762. Alternatively, as shown in FIG. 29, the frictional element 880 may include a plurality of circumferentially spaced longitudinal grooves 886 around the bore of the gripping portion 882 to provide fluid paths around the bore of the gripping portion for fluid flow after the needle 830 is removed.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention as defined by the appended claims.

What is claimed is:

1. A medical device, comprising:
    a hollow housing;
    a catheter mounted on the housing;
    a needle having a sharpened tip operable between an extended position extending forwarding from the housing and a retracted position in which the sharpened tip of the needle is enclosed in the housing;
    a biasing element biasing the needle toward the retracted position; and
    a lever mounted on the housing, pivotable between a locked positioned and an unlocked position, wherein the lever has a forward portion and a rearward portion, the forward portion directly engaging the catheter preventing the lever from pivoting into the unlocked position, and the rearward portion being connected with the rearward end of the needle retaining the needle against the bias of the biasing element;
    wherein upon removal of the catheter from the housing the catheter disengages the lever allowing the lever to pivot into the unlocked position thereby releasing the needle and the biasing element propels the needle rearwardly into the housing.

2. The medical device of claim 1 wherein the catheter is operable between a mounted position in which the catheter is mounted on the housing, and a removed position in which the catheter is removed from the housing, wherein the device comprises an indicator associated with the catheter operable to provide an indication signal when the catheter is displaced into a position intermediate the mounted position and the removed position.

3. The medical device of claim 2 wherein the indication signal is audible or tactile.

4. The medical device of claim 2 wherein the indication signal is visual.

5. The medical device of claim 2 wherein the indicator comprises a recess in the catheter that cooperates with the lever.

6. The medical device of claim 1 wherein catheter has an internal surface and an external surface, and the forward portion of the lever engages the catheter external surface.

7. The medical device of claim 1 comprising a fluid chamber in fluid communication with the needle.

8. The medical device of claim 1 wherein the lever is fixedly connected to the housing.

9. The medical device of claim 1 comprising a guard for preventing manual operation of at least a part of the rearward portion of the lever.

10. The medical device of claim 1 wherein the rearward portion of the lever is spaced rearwardly from the catheter.

11. A medical device comprising:
 a body;
 a needle projecting from the body;
 a releasable member removably attached to the body;
 a needle retainer engaging the releasably member, comprising a pivotable arm operable between a locked positioned and a released position, the needle retainer engaging the needle when the arm is in the locked position so that the needle projects forwardly from the body, and the needle retainer releasing the needle when the arm is in the released position, wherein the needle retainer is biased toward the released position; and
 a biasing element biasing the needle rearwardly,
 wherein the releasable member impedes movement of the arm into the released position and removal of the releasable member allows the arm to pivot into the released position.

12. The medical device of claim 11 wherein the needle retainer comprises a forward portion engaging the releasable member and a rearward portion retaining the needle, wherein the rearward portion is spaced rearwardly from the releasable member.

13. The medical device of claim 12 wherein at least part of the rearward portion projects into the housing.

14. The medical device of claim 12 wherein the forward portion and the rearward portion of the needle retainer are integral.

15. The medial device of claim 12 comprising a guard for preventing manual operation of at least part of the rearward portion of the needle retainer.

16. The medical device of claim 12 wherein the catheter has an internal surface and an external surface and the forward portion of the needle retainer engages the catheter external surface.

17. The medical device of claim 11 wherein the catheter is operable between a mounted position in which the catheter is mounted on the housing, and a removed position in which the catheter is removed from the housing, wherein the device comprises an indicator associated with the catheter operable to provide an indication signal when the catheter is displaced into a position intermediate the mounted position and the removed position.

18. The medical device of claim 17 wherein the indication signal is audible or tactile.

19. The medical device of claim 17 wherein the indication signal is visual.

20. The medical device of claim 17 wherein the indicator comprises a recess in the catheter that cooperates with the needle retainer.

21. The medical device of claim 11 wherein the releasable member is a catheter.

22. The medical device of claim 11 comprising a fluid chamber in fluid communication with the needle.

23. The medical device of claim 11 wherein the needle retainer is fixedly connected to the housing.

24. The medical device of claim 11 wherein the biasing element is fixedly connected to the needle.

25. The medical device of claim 11 wherein the rearward portion of the needle retainer comprises a latch for engaging the needle.

26. A medical device, comprising:
 a housing;
 a catheter removably mounted on the housing;
 an insertion needle;
 a needle retainer releasably retaining the insertion needle projecting forwardly from the housing, wherein the needle retainer is constrained to pivotable motion prior to retraction, the needle retainer comprising:
  a forward portion engaging the catheter; and
  a rearward portion connected with the needle;
 a biasing element biasing the needle rearwardly;
 wherein the needle retainer releases the needle upon removal of the catheter from the housing such that the biasing element propels the needle rearwardly.

27. The medical device of claim 26 wherein the catheter is operable between a mounted position in which the catheter is mounted on the housing, and a removed position in which the catheter is removed from the housing, wherein the device comprises an indicator associated with the catheter operable to provide an indication signal when the catheter is displaced into a position intermediate the mounted position and the removed position.

28. The medical device of claim 27 wherein the indication signal is audible or tactile.

29. The medical device of claim 27 wherein the indication signal is visual.

30. The medical device of claim 27 wherein the indicator comprises a recess in the catheter that cooperates with the needle retainer.

31. The medical device of claim 26 wherein the rearward portion of the needle retainer is spaced rearwardly from the catheter.

32. The medical device of claim 26 wherein at least part of the rearward portion of the needle retainer projects into the housing.

33. The medical device of claim 26 wherein the forward portion and the rearward portion of the needle retainer are integral.

34. The medical device of claim 26 comprising a fluid chamber in fluid communication with the needle.

35. The medical device of claim 26 wherein the housing is hollow and the housing has a rearward end that is substantially closed.

36. The medical device of claim 26 wherein the needle retainer is fixedly connected to the housing.

37. The medical device of claim 26 wherein the rearward portion of the needle retainer comprises a latch for engaging the needle.

38. The medical device of claim 26 wherein the catheter has an internal surface and an external surface and the forward portion engages the catheter external surface.

39. The medical device of claim 26 comprising a guard for preventing manual operation of at least part of the rearward portion of the needle retainer.

40. The medical device of claim 26 wherein the forward portion and the rearward portion of the needle retainer are integral.

41. A medical device, comprising:
- a catheter having an internal surface and an external surface;
- a housing onto which the catheter is removably mounted;
- a needle projecting forwardly from the housing;
- a biasing element biasing the needle rearwardly;
- a needle retainer having a first portion engaging the catheter external surface and a second portion connected with the needle, wherein the needle retainer is constrained to pivotable motion prior to retraction;
- wherein the needle retainer releases the needle in response to removal of the catheter from the housing so that the biasing element propels the needle rearwardly into the housing.

42. The medical device of claim 41 wherein the catheter is operable between a mounted position in which the catheter is mounted on the housing, and a removed position in which the catheter is removed from the housing, wherein the device comprises an indicator associated with the catheter operable to provide an indication signal when the catheter is displaced into a position intermediate the mounted position and the removed position.

43. The medical device of claim 42 wherein the indication signal is audible or tactile.

44. The medical device of claim 42 wherein the indication signal is visual.

45. The medical device of claim 42 wherein the indicator comprises a recess in the catheter that cooperates with the forward portion of the lever.

46. The medical device of claim 41 wherein the first portion and the second portion of the needle retainer are integral.

47. The medical device of claim 41 wherein the second portion of the needle retainer is spaced rearwardly from the catheter.

48. The medical device of claim 41 wherein at least part of the second portion of the needle retainer projects into the housing.

49. The medical device of claim 41 comprising a fluid chamber in fluid communication with the needle.

50. The medical device of claim 41 wherein the needle retainer is fixedly connected to the housing.

51. The medical device of claim 41 wherein the biasing element is fixedly connected to the needle.

52. The medical device of claim 41 comprising a guard for preventing manual operation of at least part of the second portion of the needle retainer.

* * * * *